(12) United States Patent
Burke

(10) Patent No.: US 8,629,099 B2
(45) Date of Patent: Jan. 14, 2014

(54) OPHTHALMIC COMPOSITIONS COMPRISING A DIPEPTIDE

(75) Inventor: Susan E. Burke, Batavia, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 735 days.

(21) Appl. No.: 12/054,577

(22) Filed: Mar. 25, 2008

(65) Prior Publication Data
US 2009/0247469 A1 Oct. 1, 2009

(51) Int. Cl.
*A01N 37/18* (2006.01)
*A61K 31/74* (2006.01)

(52) U.S. Cl.
USPC .......................... 514/2.3; 424/78.04

(58) Field of Classification Search
USPC .......................... 424/78.04; 514/2.3
See application file for complete search history.

(56) References Cited

U.S. PATENT DOCUMENTS

| | | | |
|---|---|---|---|
| 4,409,205 A | 10/1983 | Shively | |
| 4,758,595 A | 7/1988 | Ogunbiyi et al. | |
| 4,820,352 A | 4/1989 | Riedhammer et al. | |
| 5,209,927 A | 5/1993 | Gressel et al. | |
| 5,244,799 A | 9/1993 | Anderson | |
| 5,294,607 A | 3/1994 | Glonek et al. | |
| 5,300,296 A | 4/1994 | Holly et al. | |
| 5,342,620 A | 8/1994 | Chowhan | |
| 5,494,937 A | 2/1996 | Asgharian et al. | |
| 5,505,953 A | 4/1996 | Chowhan | |
| 5,741,817 A | 4/1998 | Chowhan et al. | |
| 5,765,579 A | 6/1998 | Heiler et al. | |
| 5,800,807 A * | 9/1998 | Hu et al. | 424/78.04 |
| 6,143,799 A | 11/2000 | Chowhan et al. | |
| 6,331,523 B1 * | 12/2001 | Kljavin et al. | 514/12 |
| 6,365,636 B1 | 4/2002 | Chowhan et al. | |
| 6,429,220 B1 * | 8/2002 | Yagi et al. | 514/372 |
| 6,503,497 B2 | 1/2003 | Chowhan et al. | |
| 6,528,465 B1 | 3/2003 | Cantoro | |
| 6,620,797 B2 * | 9/2003 | Chowhan et al. | 514/57 |
| 6,765,579 B2 | 7/2004 | Champion | |
| 6,806,243 B2 | 10/2004 | Hozumi et al. | |
| 6,995,123 B2 | 2/2006 | Ketelson et al. | |
| 2002/0010154 A1 * | 1/2002 | Uchiyama et al. | 514/58 |
| 2002/0142346 A1 * | 10/2002 | Nestor et al. | 435/7.1 |
| 2003/0153622 A1 | 8/2003 | Hozumi et al. | |
| 2004/0071769 A1 | 4/2004 | Farng et al. | |
| 2004/0132704 A1 * | 7/2004 | Yanni et al. | 514/179 |
| 2004/0137079 A1 | 7/2004 | Cook et al. | |
| 2004/0253280 A1 * | 12/2004 | Chowhan et al. | 424/400 |
| 2005/0074467 A1 | 4/2005 | Fujita et al. | |
| 2005/0137166 A1 * | 6/2005 | Asgharian et al. | 514/54 |
| 2005/0260280 A1 | 11/2005 | Cook et al. | |
| 2006/0122080 A1 | 6/2006 | Mori | |
| 2006/0127496 A1 | 6/2006 | Smith | |
| 2007/0149428 A1 | 6/2007 | Ammon, Jr. et al. | |
| 2008/0095754 A1 | 4/2008 | Burke et al. | |

FOREIGN PATENT DOCUMENTS

| | | |
|---|---|---|
| EP | 0923950 A2 | 6/1999 |
| JP | 2005/346099 A | 12/2005 |
| WO | WO 95/30414 A1 | 11/1995 |
| WO | WO 96/03484 A1 | 2/1996 |
| WO | WO 98/32421 A1 | 7/1998 |
| WO | WO 02/49615 A2 | 6/2002 |
| WO | WO 03/006046 A1 | 1/2003 |
| WO | WO 2006/055454 A2 | 5/2006 |
| WO | WO 2008/049043 A2 | 4/2008 |

OTHER PUBLICATIONS

BASF website: Tetronic 904 at: http://worldaccount.basf.com/wa/NAFTA~en_US/Catalog/ChemicalsNAFTA/pi/BASF/Brand/tetronic—accessed Apr. 3, 2009.*
U.S. Appl. No. 11/854,608, filed Sep. 13, 2007.
Intl. Search Report and Opinion, "PCT/US2007/081714,".

* cited by examiner

*Primary Examiner* — Frederick Krass
*Assistant Examiner* — Adam C Milligan
(74) *Attorney, Agent, or Firm* — Toan P. Vo; Joseph Barrera

(57) ABSTRACT

An ophthalmic composition comprising one or more antimicrobial components and a dipeptide. The dipeptide comprises a glycine moiety and another amino acid moiety other than glycine. The ophthalmic compositions include contact lens care solutions for cleaning and disinfecting contact lenses.

16 Claims, No Drawings

OPHTHALMIC COMPOSITIONS COMPRISING A DIPEPTIDE

FIELD OF THE INVENTION

The invention relates to ophthalmic compositions, and in particular, a contact lens care solution, comprising a dipeptide. The dipeptide includes a glycine moiety and another amino acid moiety other than glycine.

BACKGROUND OF THE INVENTION

During normal use, contact lenses are soiled or contaminated with a wide variety of compounds that can degrade lens performance. For example, a contact lens will become soiled with biological materials such as proteins or lipids present in the tear fluid and which adhere to the lens surface. Also, by handling of the contact lens, sebum (skin oil), cosmetics or other materials can soil the contact lens. These contaminants can affect visual acuity and patient comfort. Accordingly, it is important to remove any debris from the lens surface and to disinfect the lens for safe and comfortable use. A care regimen for contact lenses typically involves both disinfection and cleaning.

For disinfection, a lens care solution must contain one or more antimicrobial components. Presently, the two most popular disinfectant components are poly(hexamethylene biguanide), at times referred to as PHMB or PAPB, and polyquaternium-1. Lens care solutions with PHMB represent a significant improvement in patient comfort and antimicrobial effectiveness compared to most other known antimicrobial components. However, as with any antimicrobial component there remains a tradeoff between the concentration of the PHMB in the solution and the comfort experienced by the patient. Due to its wide commercial acceptance, extensive efforts have been directed to improve the antimicrobial efficacy or the comfort level to the patient by chemically modifying PHMB.

Those in the art have also focused on enhancing the biocidal efficacy of an ophthalmic composition by including a compound that enhances the biocidal efficacy of the antimicrobial component. The idea being that a relative decrease in the concentration of antimicrobial component would lead to a solution with a greater comfort profile.

The use of amino acids to enhance the antimicrobial efficacy of contact lens care compositions has previously been described. For example, U.S. Pat. No. 5,741,817 to Chowhan et al. describes a method of enhancing the antimicrobial efficacy of ophthalmic compositions with the addition of a low molecular weight amino acid to a composition that does not contain ethylenediaminetetraacetic acid or the salts thereof. The claim of enhanced antimicrobial efficacy was supported by stand-alone biocidal test data. Similar stand-alone biocidal data is presented in U.S. Pat. No. 6,806,243 to demonstrate that an ophthalmic solution containing at least one antimicrobial component in combination with at least one amino acid component and at least one acidic component has germicidal or preservative activity. PCT Publication No. 95/30414 also describes the use of one or more amino acids for improved preservative efficacy in aqueous ocular care solutions.

Despite the availability of various commercial contact lens care solutions, there is always a need to improve upon the performance of such solutions. These improved lens care solutions should be simple to use, be effective against a broad spectrum of microorganisms, be non-toxic to ocular tissues and provide a comfortable ocular environment to the patient.

SUMMARY OF THE INVENTION

The invention is directed to an ophthalmic composition comprising one or more antimicrobial components and a dipeptide. The dipeptide comprises a glycine moiety and another amino acid moiety other than glycine. The ophthalmic compositions include contact lens care solutions for cleaning and disinfecting contact lenses.

The invention is also directed to an ophthalmic composition comprising: 0.02 wt. % to 2.0 wt. % of a dipeptide. The dipeptide comprises a glycine moiety and another amino acid moiety other than glycine. The ophthalmic composition also includes a antimicrobial component selected from the group consisting of biguanides, polymeric biguanides, quaternium ammonium compounds and any one mixture thereof, and 0.005 wt. % to 0.8 wt. % of a comfort agent selected from the group consisting of hyaluronic acid, hydroxypropylmethyl cellulose, hydroxyethyl cellulose, dexpanthenol, sorbitol, propylene glycol and hydroxypropyl guar.

DETAILED DESCRIPTION OF THE INVENTION

Applicants and others at Bausch & Lomb have developed and tested numerous ophthalmic formulations for use as lens care solutions. As mentioned above, such lens care solutions must satisfy a number of functional characteristics. First, the solutions must possess the cleaning ability to remove denatured tear proteins and tear lipids as well as other external contaminants. Second, the solutions must possess significant disinfecting ability against a number of different bacteria and fungal strains. Third, the solutions must remain comfortable to the contact lens patient with minimal stinging as well as provide a platform to provide additional comfort or protection to the ocular surface. Fourth, the solutions must not cause significant shrinkage or swelling of the many different contact lens materials, which in turn can lead to loss in visual acuity and unwanted or pronounced lens movement. Lastly, to address market perceptions, the solutions should have a 2-hour superficial punctate corneal staining profile that equals or exceeds the staining profiles of present commercial lens care solutions.

In addition to all of the above characteristics, the solution must also pass a stringent test protocol that is referred by those in the art as "regimen" testing. An ophthalmic composition selectively formulated to clean and disinfect soft, silicone, hydrogel contact lenses must satisfy "regimen" testing if that composition is to obtain label approval from the Food and Drug Administration (FDA) as a no rub, contact lens cleaning and disinfecting solution. Many ophthalmic compositions during development fail to pass the regimen test with each and every silicone hydrogel contact lens in the U.S. market. For example, even OptiFree® Replenish, a commercial lens care solution with no-rub approval, consistently fails regimen testing with respect to both PureVision® and O2Optics® silicone hydrogel contact lenses. A more detailed description of the regimen test is provided under the subheading Examples in this application.

Accordingly, the invention is directed to an ophthalmic composition comprising one or more antimicrobial components and a dipeptide. The dipeptide comprises a glycine moiety and another amino acid moiety other than glycine. Some of the more common dipeptides include, but are not limited to, N-glycylserine, N-glycylhistidine, N-glycylcysteine and N-glycylaspartic acid, N-glycylalanine, N-glycylglutamic acid, N-glycylglutamine, N-glycylproline, N-glycylvaline and N-glycyltyrosine. The dipeptide is present in the composition at a concentration from 0.05 wt. % to 2.0 wt. %. In one embodiment, the dipeptide is present in the composition at a concentration from 0.1 wt. % to 1.0 wt. %.

The term "ophthalmic composition" is defined as a composition intended for application in the eye or intended for treating a device to be placed in contact with the eye such as a contact lens. Ophthalmic compositions can include compositions for direct placement in the eye and include eye drop solutions such as for treating dry eye or a specific ocular condition. Ophthalmic compositions also include those compositions formulated as multi-purpose solutions for cleaning and disinfecting contact lenses or to package contact lenses.

The dipeptide present in the ophthalmic compositions can often enhance the biocidal efficacy of the composition. In many of the compositions, the dipeptide can also function as a buffering component. Two of the more preferred dipeptides are N-glycylserine and N-glycylhistidine As stated, the compositions will also include an antimicrobial component selected from quaternary ammonium compounds, biguanides and the respective polymers of each thereof. For example, biguanides include the free bases or salts of alexidine, chlorhexidine, hexamethylene biguanides and their polymers. The salts of alexidine and chlorhexidine can be either organic or inorganic and include gluconates, nitrates, acetates, phosphates, sulfates, halides and the like.

In one embodiment, the composition will include a polymeric biguanide known as poly(hexamethylene biguanide) (PHMB or PAPB) commercially available from Zeneca, Wilmington, Del. under the trademark Cosmocil™ CQ. The PHMB is present in the compositions from 0.2 ppm to 5 ppm or from 0.2 ppm to 3 ppm.

The more common quaternary ammonium compounds are generally referred to in the art as "polyquaternium" disinfectants, and are identified by a particular number following the designation such as polyquaternium-1, polyquaternium-10 or polyquaternium-42. One of the more common quaternary ammonium compounds is α-[4-tris(2-hydroxyethyl)-ammonium chloride-2-butenyl]poly[1-dimethyl ammonium chloride-2-butenyl]-ω-tris(2-hydroxyethyl)ammonium chloride, also referred to in the art as polyquaternium-1. Polyquaternium-1 is present in the ophthalmic compositions from 0.5 ppm to 15 ppm. Polyquaternium-42 is also one of the more preferred polyquaternium disinfectants, see, U.S. Pat. No. 5,300,296. Polyquaternium-42 is present in the ophthalmic compositions from 5 ppm to 50 ppm.

It is to be understood by those in the art that the compositions can include one or more of the antimicrobial components described above. For example, in one embodiment, the ophthalmic compositions include polyquaternium-1 in combination with a biguanide antimicrobial component such as poly(hexamethylene biguanide). The polyquaternium-1 is present in relatively low concentrations, that is, from 0.5 ppm to 5 ppm, relative to the reported concentration of polyquaternium-1 in both Opti-Free® and Opti-Free®Replenish. Applicants believe that the polyquaternium-1 and the PHMB, in combination, may enhance the biocidal efficacy of the ophthalmic compositions.

Contact Lens Care Compositions

The lens care solutions will also include one or more of the following components: a surfactant component, a comfort agent, a chelating or sequestering component, a buffering system and a tonicity component. The additional component or components can be selected from compounds that are known to be useful in contact lens care solutions, each of which is present in an amount effective to provide the desired functional characteristic.

One preferred surfactant class are the nonionic surfactants. The surfactant should be soluble in the lens care solution and non-irritating to eye tissues. Many nonionic surfactants comprise one or more chains or polymeric components having oxyalkylene (—O—R—) repeats units wherein R has 2 to 6 carbon atoms. Preferred nonionic surfactants comprise block polymers of two or more different kinds of oxyalkylene repeat units with the molar ratio of the different repeat units determining the HLB value of the surfactant. Satisfactory nonionic surfactants include polyethylene glycol esters of fatty acids, e.g. coconut, polysorbate, polyoxyethylene or polyoxypropylene ethers of higher alkanes ($C_{12}$-$C_{18}$). Examples of this class include polysorbate 20 (available under the trademark Tween® 20), polyoxyethylene (23) lauryl ether (Brij® 35), polyoxyethyene (40) stearate (Myrj®52), polyoxyethylene (25) propylene glycol stearate (Atlas® G 2612). Still another preferred nonionic surfactant is tyloxapol.

A particular nonionic surfactant consisting of a poly(oxypropylene)-poly(oxyethylene) adduct of ethylene diamine having a molecular weight from about 6,000 to about 24,000 daltons wherein at least 40 weight percent of said adduct is poly(oxyethylene) has been found to be particularly advantageous for use in cleaning and conditioning both soft and hard contact lenses. The CTFA Cosmetic Ingredient Dictionary's adopted name for this group of surfactants is poloxamine. Such surfactants are available from BASF Wyandotte Corp., Wyandotte, Mich., under Tetronic®. Particularly good results are obtained with poloxamine 1107 or poloxamine 1304. The poloxamine-type surfactants will generally be present in a total amount from 0.1 to 2% w/v, from 0.1 to 1% w/v, or from 0.2 to 0.8% w/v An analogous series of poly(oxyethylene) poly(oxypropylene) block polymer surfactants is the poloxamer series. Such surfactants are also available from BASF available under Pluronic®. The poloxamer series of surfactants will have molecular weights from 2500 to 13,000 daltons or from 6000 to about 12,000 daltons. Specific examples of surfactants which are satisfactory include: poloxamer 108, poloxamer 188, poloxamer 237, poloxamer 238, poloxamer 288 and poloxamer 407. Particularly good results are obtained with poloxamer 237 or poloxamer 407. The poloxamer series of surfactants are present in an amount from 0.1 to 2% w/v, from 0.1 to 1% w/v, or from 0.2 to 0.8% w/v.

Another preferred class of surfactants are the amphoteric surfactants of general formula I:

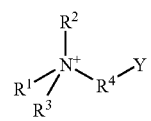

I wherein $R^1$ is R or —$(CH_2)_n$—NHC(O)R, wherein R is a $C_8$-$C_{30}$alkyl optionally substituted with hydroxyl and n is 2, 3 or 4; $R^2$ and $R^3$ are each independently selected from the group consisting of hydrogen and $C_1$-$C_4$alkyl; $R^4$ is a $C_2$-$C_8$alkylene optionally substituted with hydroxyl; and Y is $CO_2^-$ or $SO_3^-$.

The amphoteric surfactants of general formula I include a class of compounds known as betaines. The betaines are characterized by a fully quaternized nitrogen atom and do not exhibit anionic properties in alkaline solutions, which means that betaines are present only as zwitterions at near neutral pH. The amphoteric surfactants of general formula I are generally present in the compositions from 0.01 wt. % to 2.0 wt. % or from 0.05 wt. % to 1.0 wt. %.

All betaines are characterized by a fully quaternized nitrogen. In alkyl betaines, one of the alkyl groups of the quaternized nitrogen is an alkyl chain with eight to thirty carbon atoms. One class of betaines is the sulfobetaines or hydroxysulfobetaines in which the carboxylic group of alkyl betaine is replaced by sulfonate. In hydroxysulfobetaines a hydroxy- group is positioned on one of the alkylene carbons that extend from the quaternized nitrogen to the sulfonate. In alkylamido betaines, an amide group is inserted as a link between the hydrophobic $C_8$-$C_{30}$alkyl chain and the quaternized nitrogen.

In many embodiments, the amphoteric surfactant of general formula I is a sulfobetaine of general formula II

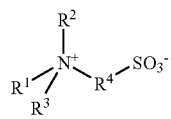

II wherein $R^1$ is a $C_8$-$C_{30}$alkyl; $R^2$ and $R^3$ are each independently selected from a $C_1$-$C_4$alkyl; and $R^4$ is a $C_2$-$C_8$alkylene.

Certain sulfobetaines of general formula II are more preferred than others. For example, Zwitergent®3-10 available from Calbiochem Company, is a sulfobetaine of general formula I wherein $R^1$ is a straight, saturated alkyl with ten (10) carbons, $R^2$ and $R^3$ are each methyl and $R^4$ is —$CH_2CH_2CH_2$— (three carbons, (3)). Other sulfobetaines that can be used in the ophthalmic compositions include the corresponding Zwitergent®3-08 ($R^1$ is a is a straight, saturated alkyl with eight carbons), Zwitergent®3-12 ($R^1$ is a is a straight, saturated alkyl with twelve carbons), Zwitergent®3-14 ($R^1$ is a is a straight, saturated alkyl with fourteen carbons) and Zwitergent®3-16 ($R^1$ is a is a straight, saturated alkyl with sixteen carbons). Accordingly, some of the more preferred the ophthalmic composition will include a sulfobetaine of general formula II wherein $R^1$ is a $C_8$-$C_{16}$alkyl and $R^2$ and $R^3$ is methyl.

In another embodiment, the amphoteric surfactant of general formula I is a hydroxysulfobetaine of general formula III

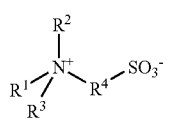

III wherein $R^1$ is a $C_8$-$C_{30}$alkyl substituted with at least one hydroxyl; $R^2$ and $R^3$ are each independently selected from a $C_1$-$C_4$alkyl; and $R^4$ is a $C_2$-$C_8$alkylene substituted with at least one hydroxyl.

In another embodiment, the amphoteric surfactant is an alkylamido betaine of general formula IV

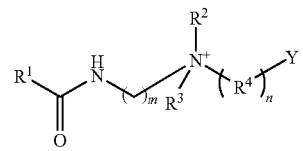

IV wherein $R^1$ is a $C_8$-$C_{30}$alkyl, and m and n are independently selected from 2, 3, 4 or 5; $R^2$ and $R^3$ are each independently selected from a $C_1$-$C_4$alkyl optionally substituted with hydroxyl; $R^4$ is a $C_2$-$C_8$alkylene optionally substituted with hydroxyl; and Y is $CO_2^-$ or $SO_3^-$. The most common alkylamido betaines are alkylamidopropyl betaines, e.g., cocoamidopropyl dimethyl betaine and lauroyl amidopropyl dimethyl betaine.

The lens care solutions can also include a phosphonic acid, or its physiologically compatible salt, that is represented by the following formula:

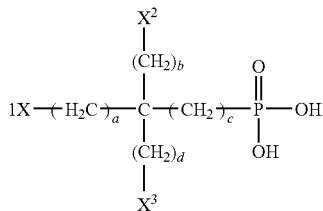

wherein each of a, b, c, and d are independently selected from integers from 0 to 4, preferably 0 or 1; $X^1$ is a phosphonic acid group (i.e., $P(OH)_2O$), hydroxy, amine or hydrogen; and $X^2$ and $X^3$ are independently selected from the group consisting of halogen, hydroxy, amine, carboxy, alkylcarbonyl, alkoxycarbonyl, or substituted or unsubstituted phenyl, and methyl. Exemplary substituents on the phenyl are halogen, hydroxy, amine, carboxy and/or alkyl groups. A particularly preferred species is that wherein a, b, c, and d in are zero, specifically the tetrasodium salt of 1-hydroxyethylidene-1,1-diphosphonic acid, also referred to as tetrasodium etidronate, commercially available from Monsanto Company as DeQuest® 2016 diphosphonic acid sodium salt or phosphonate.

A lens care solution will likely include a comfort component. A comfort component can provide any number of desired characteristics to enhance patient comfort including maintaining a level of hydration of the ocular surface, providing a cushioning effect, alleviatating ocular irritation or promoting tear film stability. The comfort component can also enhance and/or prolong the cleaning and wetting activity of the surfactant component and/or condition the lens surface rendering it more hydrophilic (less lipophilic) and/or act as a demulcent on the eye.

One particular comfort agent that demonstrates an exceptional comfort profile is hyaluronic acid. Hyaluronic acid is a linear polysaccharide (long-chain biological polymer) formed by repeating disaccharide units consisting of D-glucuronic acid and N-acetyl-D-glucosamine linked by β(1-3) and β(1-4) glycosidic linkages. Hyaluronic acid is distinguished from the other glycosaminoglycans, as it is free from covalent links to protein and sulphonic groups. Hyaluronic acid is ubiquitous in animals, with the highest concentration found in soft connective tissue. It plays an important role for both mechanical and transport purposes in the body; e.g., it gives elasticity to the joints and rigidity to the vertebrate disks, and it is also an important component of the vitreous body of the eye.

Hyaluronic acid is accepted by the ophthalmic community as a compound that can protect biological tissues or cells from compressive forces. Accordingly, hyaluronic acid has been proposed as one component of a viscoelastic ophthalmic composition for cataract surgery. The viscoelastic properties of hyaluronic acid, that is, hard elastic under static conditions though less viscous under small shear forces enables hyaluronic acid to basically function as a shock absorber for cells and tissues. Hyaluronic acid also has a relatively large capacity to absorb and hold water. The stated properties of hyaluronic acid are dependent on the molecular weight, the solution concentration, and physiological pH. At low concentrations, the individual chains entangle and form a continuous network in solution, which gives the system interesting properties, such as pronounced viscoelasticity and pseudoplasticity that is unique for a water-soluble polymer at low concentration.

It is to be understood by one of ordinary skill in the art that the term "hyaluronic acid" includes the corresponding acid salts, e.g, the sodium, calcium or zinc salts of hyaluronic acid.

The hyaluronic acid and the PHMB are each present in the ophthalmic compositions over a relatively limited concentration range. If the concentration of the hyaluronic acid is below 0.002 wt. % the commercial characteristics of added patient comfort is virtually absent. If, on the other hand, the hyaluronic acid concentration is about 0.02 wt. % and the PHMB concentration is about 1 to about 1.3 ppm, one begins to observe a decrease in the biocidal efficacy of the compositions over time, and in particular, with respect to the microorganism, C. albicans. In many of the compositions, the hyaluronic acid concentration is from 0.0075 wt. % to 0.015 wt. % and the PHMB concentration is from 0.8 ppm to 2.0 ppm.

Another known comfort agent is dexpanthenol, which is an alcohol of pantothenic acid, also called Provitamin B5, D-pantothenyl alcohol or D-panthenol. It has been stated that dexpanthenol may play a role in stabilizing the lachrymal film at the eye surface following placement of a contact lens on the eye. Dexpanthenol is preferably present in the solution in an amount from 0.2 to 5.0% w/v, from 0.5 to 3.0% w/v, or from 0.5 to 2.0% w/v.

The contact lens care solutions can also include a sugar alcohol such as sorbitol or xylitol. Typically, dexpanthenol is used in combination with the sugar alcohol. The sugar alcohol is present in the lens care compositions in an amount from 0.4 to 5% w/v or from 0.8 to 3% w/v.

The lens care solutions can also include one or more neutral or basic amino acids. The neutral amino acids include: the alkyl-group-containing amino acids such as alanine, isoleucine, valine, leucine and proline; hydroxyl-group-containing amino acids such as serine, threonine and 4-hydroxyproline; thio-group-containing amino acids such as cysteine, methionine and asparagine. Examples of the basic amino acid include lysine, histidine and arginine. The one or more neutral or basic amino acids are present in the compositions at a total concentration of from 0.1 to 3% w/v.

The lens care solutions can also include glycolic acid, asparatic acid or any mixture of the two at a total concentration of from 0.001% to 4% (w/v) or from 0.01% to 2.0% (w/v). In addition, the combined use of one or more amino acids and glycolic acid and/or asparatic acid can lead to a reduction in the change of the size of the contact lens due to swelling and shrinkage following placement in the lens solution.

The ophthalmic composition can also include 2-amino-2-methyl-1,3-propanediol or a salt thereof (AMPD). Preferably, the AMPD is added to the solutions in an amount to satisfy a predetermined molar ratio of glycolic acid, asparatic acid, α-hydroxy acid or any mixture thereof and AMPD. The molar ratio of glycolic acid, asparatic acid, α-hydroxy acid or any mixture thereof to AMPD is 1:20 to 1.3:1, from 1:15 to 1.2:1 or from 1:14 to 1:1. The glycolic acid, asparatic acid, α-hydroxy acid or any mixture thereof is present in the ophthalmic compositions at a concentration of 0.01% to 5% (w/v) or at a concentration of 0.05% to 1% (w/v).

Other suitable comfort components include, but are not limited to, water soluble natural gums, cellulose-derived polymers and the like. Useful natural gums include guar gum, gum tragacanth and the like. Useful cellulose-derived comfort components include cellulose-derived polymers, such as hydroxypropyl cellulose, hydroxypropylmethyl cellulose, carboxymethyl cellulose, methyl cellulose, hydroxyethyl cellulose and the like. A very useful comfort component is hydroxypropylmethyl cellulose (HPMC). Some non-cellulose comfort components include propylene glycol or glycerin. The comfort components are typically present in the solution from 0.005% to 0.5% (w/v).

One particular comfort agent that is believed to maintain a hydrated corneal surface is polyvinylpyrrolidone (PVP). PVP is a linear homopolymer or essentially a linear homopolymer comprising at least 90% repeat units derived from 1-vinyl-2-pyrrolidone monomer, the remainder of the monomer composition can include neutral monomer, e.g., vinyl or acrylates. Other synonyms for PVP include povidone, polyvidone, 1-vinyl-2-pyrolidinone, and 1-ethenyl-2-pyrolionone (CAS registry number 9003-39-8). The PVP will preferably have a weight average molecular weight from 10,000 to 250,000 or from 30,000 to 100,000. Such materials are sold by various companies, including ISP Technologies, Inc. under the trademark PLASDONE®K-29/32, from BASF under the trademark KOLLIDON®, for example, KOLLIDON® K-30 or K-90. It is also preferred that one use pharmaceutical grade PVP.

Many of the dipeptides present in the ophthalmic compositions can also function as a buffer component in the physiological pH range whereas the individual component amino acids cannot because of a shift in the $pK_a$ of the acid-base functional groups upon formation of the dipeptide bond. For example, the $pK_a$ values for glycine are 2.4 and 9.8, while those for serine are 2.2 and 9.2. However, the $pK_a$ values for N-glycylserine are calculated to be 3.0 and 8.3. The following Table illustrates the pK of the above illustrated dipeptides and their corresponding amino acid components.

As indicated by the Table of pK values, the inclusion a dipeptide lowers the pKa values for the amine functionality so that it is closer to 8. Accordingly, the dipeptides can often play a role in maintaining the pH of the compositions in a range from 7 to 9.

| Compound | $pK_b$ of COOH | $pK_a$ of $NH_3+$ |
| --- | --- | --- |
| N-glycylaspartic acid | 2.92 | 8.34 |
| N-glycylhistidine | 2.95 | 8.23 |
| N-glycylcysteine | 2.86 | 8.21 |
| N-glycylserine | 2.97 | 8.33 |
| glycine | 2.43 | 9.64 |
| aspartic acid | 2.28 | 9.95 |
| histidine | 1.91 | 9.53 |
| cysteine | 2.07 | 10.25 |
| serine | 2.16 | 9.10 |

Although the dipeptide present in the ophthalmic compositions can function as a buffer in a physiological pH range, the compositions are likely to include additional buffering components or a buffer system known to be useful in contact lens care solutions. By the terms "buffer component" or "buffer system" is meant a compound that, usually in combination with at least one other compound, provides a buffering system in solution that exhibits buffering capacity, that is, the capacity to neutralize, within limits, either acids or bases (alkali) with relatively little or no change in the original pH. Generally, the buffering components are present from 0.05% to 2.5% (w/v) or from 0.1% to 1.5% (w/v).

The term "buffering capacity" is defined to mean the millimoles (mM) of strong acid or base (or respectively, hydrogen or hydroxide ions) required to change the pH by one unit when added to one liter (a standard unit) of the buffer solution. The buffer capacity will depend on the type and concentration of the buffer components. The buffer capacity is measured from a starting pH of 6 to 8, preferably from 7.4 to 8.4.

Borate buffers include, for example, boric acid and its salts, for example, sodium borate or potassium borate. Borate buffers also include compounds such as potassium tetraborate or potassium metaborate that produce borate acid or its salt in solutions. Borate buffers are known for enhancing the efficacy of certain polymeric biguanides. For example, U.S. Pat. No. 4,758,595 to Ogunbiyi et al. describes that a contact-lens solution containing PHMB can exhibit enhanced efficacy if combined with a borate buffer.

A phosphate buffer system preferably includes one or more monobasic phosphates, dibasic phosphates and the like. Particularly useful phosphate buffers are those selected from phosphate salts of alkali and/or alkaline earth metals. Examples of suitable phosphate buffers include one or more of sodium dibasic phosphate ($Na_2HPO_4$), sodium monobasic phosphate ($NaH_2PO_4$) and potassium monobasic phosphate ($KH_2PO_4$). The phosphate buffer components frequently are used in amounts from 0.01% or to 0.5% (w/v), calculated as phosphate ion.

Other known buffer compounds can optionally be added to the lens care compositions, for example, citrates, citric acid, sodium bicarbonate, TRIS, and the like. Other ingredients in the solution, while having other functions, may also affect the buffer capacity, e.g., propylene glycol or glycerin.

A preferred buffer system is based upon boric acid/borate, a mono and/or dibasic phosphate salt/phosphoric acid or a combined boric/phosphate buffer system. For example a combined boric/phosphate buffer system can be formulated from a mixture of boric acid/sodium borate and a monobasic/dibasic phosphate. In a combined boric/phosphate buffer system, the phosphate buffer is used (in total) at a concentration of 0.004 to 0.2 M (Molar), preferably 0.04 to 0.1 M. The borate buffer (in total) is used at a concentration of 0.02 to 0.8 M, preferably 0.07 to 0.2 M.

The lens care solutions can also include one or more chelating components to assist in the removal of lipid and protein deposits from the lens surface following daily use. Typically, the ophthalmic compositions will include relatively low amounts, e.g., from 0.005% to 0.05% (w/v) of ethylenediaminetetraacetic acid (EDTA) or the corresponding metal salts thereof such as the disodium salt, $Na_2EDTA$.

One possible alternative to the chelator $Na_2EDTA$ or a possible combination with $Na_2EDTA$, is a disuccinate of formula IV below or a corresponding salt thereof;

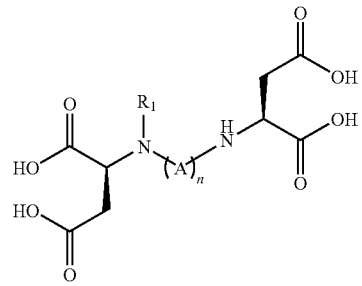

wherein $R_1$ is selected from hydrogen, alkyl or —C(O) alkyl, the alkyl having one to twelve carbons and optionally one or more oxygen atoms, A is a methylene group or an oxyalkylene group, and n is from 2 to 8. In one embodiment, the disuccinate is S,S-ethylenediamine disuccinate (S,S-EDDS) or a corresponding salt thereof. One commercial source of S,S-EDDS is represented by Octaquest® E30, which is commercially available from Octel. The chemical structure of the trisodium salt of S,S-EDDS is shown below. The salts can also include the alkaline earth metals such as calcium or magnesium. The zinc or silver salt of the disuccinate can also be used in the ophthalmic compositions.

Still another class of chelators include alkyl ethylenediaminetriacetates such as nonayl ethylenediaminetriacetate. See, U.S. Pat. No. 6,995,123 for a more complete description of such agents.

The lens care solutions will typically include an effective amount of a tonicity adjusting component. Among the suitable tonicity adjusting components that can be used are those conventionally used in contact lens care products such as various inorganic salts. Sodium chloride and/or potassium chloride and the like are very useful tonicity components. The amount of tonicity adjusting component is effective to provide the desired degree of tonicity to the solution.

The lens care solutions will typically have an osmolality in the range of at least about 200 mOsmol/kg for example, about 300 or about 350 to about 400 mOsmol/kg. The lens care solutions are substantially isotonic or hypertonic (for example, slightly hypertonic) and are ophthalmically acceptable.

As described, the ophthalmic compositions can be used to clean and disinfect contact lenses. In general, the contact lens solutions can be used as a daily or every other day care regimen known in the art as a "no-rub" regimen. This procedure includes removing the contact lens from the eye, rinsing both sides of the lens with a few milliliters of solution and placing the lens in a lens storage case. The lens is then immersed in fresh solution for at least two hours. The lens is then removed form the case, optionally rinsed with more solution, and repositioned on the eye.

Alternatively, a rub protocol would include each of the above steps plus the step of adding a few drops of the solution to each side of the lens, followed by gently rubbing the surface between ones fingers for approximately 3 to 10 seconds. The lens can then be, optionally rinsed, and subsequently immersed in the solution for at least two hours. The lenses are removed from the lens storage case and repositioned on the eye.

One exemplary ophthalmic composition is formulated as a contact lens disinfecting solution prepared with the components and amounts of each listed in Table 1.

TABLE 1

| Component | Minimum Amount (wt. %) | Maximum Amount (wt. %) | Preferred Amount (wt. %) |
|---|---|---|---|
| boric acid | 0.10 | 1.0 | 0.64 |
| sodium borate | 0.01 | 0.20 | 0.1 |
| sodium chloride | 0.20 | 0.80 | 0.49 |
| Zwitergent ® 3-10 | 0.005 | 0.5 | 0.05 |
| N-glycylserine | 0.05 | 2.0 | 0.5 |
| Tetronic ® 1107 | 0.05 | 2.0 | 1.00 |
| Na$_2$EDTA | 0.005 | 0.15 | 0.03 |
| PHMB | 0.2 ppm | 3 ppm | 1 ppm |

Another contact lens solution according to the present invention includes the following ingredients listed in Table 2.

TABLE 2

| Component | Minimum Amount (wt. %) | Maximum Amount (wt. %) | Preferred Amount (wt. %) |
|---|---|---|---|
| sorbitol or xylitol | 0.5 | 5 | 3 |
| poloxamer 407 | 0.05 | 1.0 | 0.10 |
| sodium phosphate, dihydrogen | 0.10 | 0.8 | 0.46 |
| dexpanthenol | 0.01 | 1.0 | 0.03 |
| zwitergent ® 3-10 | 0.01 | 0.2 | 0.05 |
| N-glycylserine | 0.05 | 2.0 | 0.5 |
| Na$_2$EDTA | 0.005 | 0.3 | 0.1 |
| PHMB | 0.2 ppm | 2 ppm | 1 ppm |

Another contact lens solution according to the present invention includes the following ingredients listed in Table 3.

TABLE 3

| Component | Minimum Amount (wt. %) | Maximum Amount (wt. %) | Preferred Amount (wt. %) |
|---|---|---|---|
| propylene glycol | 0.1 | 1.0 | 0.50 |
| poloxamer 237 | 0.01 | 0.20 | 0.05 |
| phosphate monobasic | 0.05 | 0.40 | 0.10 |
| phosphate dibasic | 0.05 | 0.4 | 0.12 |
| N-glycylserine | 0.05 | 2.0 | 0.5 |
| Na$_2$EDTA | 0.005 | 0.3 | 0.1 |
| HPMC | 0.02 | 0.6 | 0.15 |
| PHMB | 0.2 ppm | 2 ppm | 1.1 ppm |

Another contact lens solution according to the present invention includes the following ingredients listed in Table 4.

TABLE 4

| Component | Minimum Amount (wt. %) | Maximum Amount (wt. %) | Preferred Amount (wt. %) |
|---|---|---|---|
| sorbitol | 0.2 | 2.0 | 0.5 |
| propylene glycol | 0.2 | 2.0 | 0.6 |
| tetronic ® 1304 | 0.01 | 0.2 | 0.05 |
| boric acid | 0.1 | 1.0 | 0.60 |
| sodium borate | 0.01 | 0.2 | 0.10 |
| hydroxypropyl guar | 0.01 | 0.5 | 0.05 |
| N-glycylserine | 0.05 | 2.0 | 0.5 |
| Na$_2$EDTA | 0.02 | 0.1 | 0.05 |
| polyquaternium-1 | 3 ppm | 15 ppm | 10 ppm |

Another contact lens solution according to the present invention includes the following ingredients listed in Table 5.

TABLE 5

| Component | Minimum Amount (wt. %) | Maximum Amount (wt. %) | Preferred Amount (wt. %) |
|---|---|---|---|
| phosphate monobasic | 0.05 | 0.40 | 0.12 |
| phosphate dibasic | 0.05 | 0.4 | 0.21 |
| sorbitol | 0.5 | 2.0 | 1.0 |
| Tetronics ® 904 | 0.02 | 0.5 | 0.10 |
| Povidone ® K90 | 0.05 | 0.5 | 0.10 |
| N-glycylserine | 0.05 | 2.0 | 0.5 |
| Na$_2$EDTA | 0.005 | 0.3 | 0.1 |
| PHMB | 0.2 ppm | 2 ppm | 1 ppm |

The ophthalmic compositions can be used with many different types of contact lenses including: (1) hard lenses formed from materials prepared by polymerization of acrylic esters, such as poly(methyl methacrylate) (PMMA), (2) rigid gas permeable (RGP) lenses formed from silicone acrylates and fluorosilicone methacrylates, (3) soft, hydrogel lenses, and (4) non-hydrogel elastomer lenses.

As an example, soft hydrogel contact lenses are made of a hydrogel polymeric material, a hydrogel being defined as a crosslinked polymeric system containing water in an equilibrium state. In general, hydrogels exhibit excellent biocompatibility properties, i.e., the property of being biologically or biochemically compatible by not producing a toxic, injurious or immunological response in a living tissue. Representative conventional hydrogel contact lens materials are made by polymerizing a monomer mixture comprising at least one hydrophilic monomer, such as (meth)acrylic acid, 2-hydroxyethyl methacrylate (HEMA), glyceryl methacrylate, N,N-dimethacrylamide, and N-vinylpyrrolidone (NVP). In the case of silicone hydrogels, the monomer mixture from which the copolymer is prepared further includes a silicone-containing monomer, in addition to the hydrophilic monomer. Generally, the monomer mixture will also include a crosslink monomer such as ethylene glycol dimethacrylate, tetraethylene glycol dimethacrylate, and methacryloxyethyl vinylcarbonate. Alternatively, either the silicone-containing monomer or the hydrophilic monomer may function as a crosslink agent.

The ophthalmic compositions can also be formulated as a contact lens rewetting eye drop solution. By way of example, the rewetting drops may be reformulated from a lens care solution by reducing the amount of antimicrobial agent to a preservative amount and/or by adding an additional humectant and/or demulcent.

The ophthalmic compositions can be used as a preservative in formulations for treating patients with dry eye. In such a method, the ophthalmic composition is administered to the patient's eye, eye lid or to the skin surrounding the patient's eye. The compositions can be administered to the eyes irrespective of whether contact lenses are present in the eyes of the patient. For example, many people suffer from temporary or chronic eye conditions in which the eye's tear system fails to provide adequate tear volume or tear film stability necessary to remove irritating environmental contaminants such as dust, pollen, or the like.

The ophthalmic compositions can also be used as a preservative in pharmaceutical compositions such as nasal sprays, ear and eye drops, suppositories, and prescription and over-the-counter formulations containing a pharmaceutical active that are used or administered over time such as a cream, ointment, gel or solution. Generally, the active pharmaceutical agent is in one or more classes of ocular pharmaceuticals including, but not limited to anti-inflammatory agents, antibiotics, immunosuppressive agents, antiviral agents, antifungal agents, anesthetics and pain killers, anticancer agents, anti-glaucoma agents, peptide and proteins, anti-allergy agents.

Although the invention can be embodied as many different compositions as described above, the compositions described is an exemplification of the principles of the invention and is not intended to limit the invention to the particular embodiments illustrated.

EXAMPLES

The invention is illustrated by the following non-limiting examples.

In demonstrating the efficacy of the addition of the dipeptides of the present invention, a Stand-Alone Biocidal Efficacy Test was used. The "Stand-Alone Procedure for Disinfecting Products" is based on the Disinfection Efficacy Testing for Products dated May 1, 1997, prepared by the U.S. Food and Drug Administration, Division of Ophthalmic Devices. This performance requirement does not contain a rub procedure. This performance requirement is comparable to current ISO standards for disinfection of contact lenses (revised 1995). The stand-alone test challenges a disinfecting product with a standard inoculum of a representative range of microorganisms and establishes the extent of viability loss at predetermined time intervals comparable with those during which the product may be used. The primary criteria for a given disinfection period (corresponding to a potential minimum recommended disinfection period) is that the number of bacteria recovered per mL must be reduced by a mean value of not less than 3.0 logs within the given disinfection period. The number of mold and yeast recovered per mL must be reduced by a mean value of not less than 1.0 log within the minimum recommended disinfection time with no increase at four times the minimum recommended disinfection time.

The antimicrobial efficacy of each of the various compositions for the chemical disinfection and cleaning of contact lenses is evaluated in the presence of 10% organic soil using the stand-alone procedure. Microbial challenge inoculums are prepared using *Staphylococcus aureus* (ATCC 6538), *Serratia marcescens* (ATT 13880) and *Candida albicans* (ATCC 10231). The test organisms are cultured on appropriate agar and the cultures are harvested using sterile Dulbecco's Phosphate Buffered Saline plus 0.05 percent weight/volume polysorbate 80 (DPBST) or a suitable diluent and transferred to a suitable vessel. Spore suspensions are filtered through sterile glass wool to remove hyphal fragments. *Serratia marcescens*, as appropriate, is filtered through a 1.2 um filter to clarify the suspension.

After harvesting, the suspension is centrifuged at no more than 5000×g for a maximum of 30 minutes at 20 to 25° C. The supernatant is then poured off and resuspended in DPBST or another suitable diluent. The suspension is centrifuged a second time and resuspended in DPBST or other suitable diluent. All challenge bacterial and fungal cell suspensions are adjusted with DPBST or other suitable diluent to $1 \times 10^7$ to $1 \times 10^8$ cfu/mL. The appropriate cell concentration can be estimated by measuring the turbidity of the suspension, for example, using a spectrophotometer at a preselected wavelength, for example, 490 nm. One tube is prepared containing a minimum of 10 mL of test solution per challenge organism. Each tube of the solution to be tested is inoculated with a suspension of the test organism sufficient to provide a final count of $1 \times 10^5$ to $1 \times 10^6$ cfu/mL (the volume of the inoculum not exceeding 1 percent of the sample volume). Dispersion of the inoculum is ensured by vortexing the sample for at least 15 seconds. The inoculated product is stored at 10 to 25° C. Aliquots in the amount of 1.0 mL are taken of the inoculated product for determination of viable counts after certain time period of disinfection.

The time points for the bacteria and fungi were 1 and 4 hours. The suspension is mixed well by vortexing vigorously for at least 5 seconds. The 1.0 mL aliquots removed at the specified time intervals are subjected to a suitable series of decimal dilutions in validated neutralizing media. The suspensions are mixed vigorously and incubated for a suitable period of time to allow for neutralization of the microbial agent. The viable count of organisms is determined in appropriate dilutions by preparation of triplicate plates of trypticase soy agar (TSA) for bacteria and Sabouraud dextrose agar (SDA) for mold and yeast. The bacterial recovery plates are incubated at 30 to 35° C. for two to four days. The yeast recovery plates are incubated at 20 to 30° C. for two to four days. The mold recovery plates were incubated at 20 to 25° C. for three to seven days. The average number of colony forming units is determined on countable plates. Countable plates refer to 30 to 300 cfu/plates for bacteria and yeast and 8 to 80 cfu/plate for mold, except when colonies are observed only for the $10^0$ or $10^1$ dilution plates. The microbial reduction is then calculated at the specified time points.

In order to demonstrate the suitability of the medium used for growth of the test organisms and to provide an estimation of the initial inoculum concentration, inoculum controls are made by dispersing an identical aliquot of the inoculum into a suitable diluent, for example, DPBST, using the same volume of diluent used to suspend the organism as listed above. Following inoculation in a validated neutralizing broth and incubation for an appropriate period of time, the inoculum control must be between $1.0 \times 10^5$ and $1.0 \times 10^6$ cfu/mL.

The following Example Compositions illustrate how the use of an effective amount of a dipeptide with glycine and one other amino acid moiety other than glycine enhances the antimicrobial efficacy of an ophthalmic composition. The Example Compositions include alexidine 2HCl as an antimicrobial component in a borate buffer system Table 6. Example compositions comprising dipeptides are numeric and include N-glycylserine, N-glycylhistidine, N-glycylcysteine and N-glycylaspartic acid. Applicants also prepared and tested comparative example solutions without the dipeptide but with the corresponding amino acid component including serine, histidine, cysteine and aspartic acid. These comparative solutions are given a non-numeric code; A, B, C, D and E.

TABLE 6

| | Solution No. (% w/w) | | | | | | | | | |
|---|---|---|---|---|---|---|---|---|---|---|
| | A | B | 1 | C | 2 | D | 3 | E | 4 | control |
| boric acid | 0.223 | 0.223 | 0.223 | 0.223 | 0.223 | 0.223 | 0.223 | 0.223 | 0.223 | 0.223 |
| Na borate | 0.077 | 0.077 | 0.077 | 0.077 | 0.077 | 0.077 | 0.077 | 0.077 | 0.077 | 0.077 |
| glycerin | 1.0 | 1.0 | 1.0 | 1.0 | 1.0 | 1.0 | 1.0 | 1.0 | 1.0 | 1.0 |
| glycine | 0.5 | — | — | — | — | — | — | — | — | — |

TABLE 6-continued

| | A | B | 1 | C | 2 | D | 3 | E | 4 | control |
|---|---|---|---|---|---|---|---|---|---|---|
| serine | — | 0.5 | — | — | — | — | — | — | — | — |
| N-glycylserine | — | — | 0.5 | — | — | — | — | — | — | — |
| histidine | — | — | — | 0.5 | — | — | — | — | — | — |
| N-glycylhistidine | — | — | — | — | 0.5 | — | — | — | — | — |
| cysteine | — | — | — | — | — | 0.5 | — | — | — | — |
| N-glycylcysteine | — | — | — | — | — | — | 0.5 | — | — | — |
| aspartic acid | — | — | — | — | — | — | — | 0.5 | — | — |
| N-glycylaspartic acid | — | — | — | — | — | — | — | — | 0.5 | — |
| alexidine 2HCL | 0.0001 | 0.0001 | 0.0001 | 0.0001 | 0.0001 | 0.0001 | 0.0001 | 0.0001 | 0.0001 | 0.0001 |

The stand-alone biocidal data for Example Compositions 1 to 4 and comparative solutions A to E plus control are reported in Table 7. As indicated, the antimicrobial efficacy of alexdine.2HCl against *S. aureus* is significantly improved in the presence of any of the dipeptides tested (within 4 hours) in comparison to the control of alexidine 2HCl in borate buffer. In addition, the efficacy against *S. aureus* in the presence of the dipeptide is greater than that the two corresponding amino acids alone (within 4 hours). In particular, the dipeptides N-glycylserine and N-glycylhistidine, Example Compositions 1 and 2, respectively, exhibit a pronounced enhancement over the comparative solutions A, B and C with respect to *S. aureus* and *C. albicans*.

TABLE 7

Stand-alone biocidal data

| Test Solution | Time (hr) | S. auers | S. marcescens | C. albicans |
|---|---|---|---|---|
| A | 1 | 3.0 | 2.5 | 2.0 |
| | 4 | 3.4 | 3.2 | 2.4 |
| B | 1 | 2.7 | 2.3 | 1.9 |
| | 4 | 3.9 | 2.9 | 2.1 |
| 1 | 1 | 4.1 | 3.3 | 2.8 |
| | 4 | >4.6 | 4.1 | 3.8 |
| C | 1 | 3.1 | 2.0 | 1.7 |
| | 4 | 3.9 | 2.7 | 1.8 |
| 2 | 1 | 4.4 | 2.4 | 2.5 |
| | 4 | 4.6 | 3.4 | 3.4 |
| D | 1 | 1.6 | 1.1 | 0.7 |
| | 4 | 2.7 | 1.6 | 0.5 |
| 3 | 1 | 2.9 | 1.9 | 2.0 |
| | 4 | 4.1 | 2.7 | 2.3 |
| E | 1 | 3.0 | 2.6 | 2.1 |
| | 4 | 3.3 | 3.3 | 2.4 |
| 4 | 1 | 3.0 | 2.3 | 2.0 |
| | 4 | 4.1 | 2.8 | 2.0 |
| control | 1 | 3.0 | 0.7 | 0.8 |
| | 4 | 3.3 | 0.9 | 0.9 |

Experimental error ± 0.5

The above disclosure is intended to be illustrative and not exhaustive. This description will suggest many variations and alternatives to one of ordinary skill in this art. The various elements described above and claimed below can be combined or modified for combination as desired.

I claim:

1. An aqueous ophthalmic composition comprising one or more antimicrobial components selected from the group consisting of 0.2 ppm to 3 ppm poly(hexamethylene biguanide), from 0.5 ppm to 5 ppm α-[4-tris(2-hydroxyethyl)-ammonium chloride-2-butenyl]poly[1-dimethyl ammonium chloride-2-butenyl]-ω-tris(2-hydroxyethyl) ammonium chloride and alexidine, and a dipeptide, wherein the dipeptide comprises a glycine moiety and another amino acid moiety other than glycine, and the dipeptide is present in an amount to enhance the biocidal efficacy of the ophthalmic composition.

2. The ophthalmic composition according to claim 1, wherein the amount of the dipeptide further functions as a buffer in the physiological pH range.

3. The ophthalmic composition according to claim 1, wherein the dipeptide is selected from the group consisting of N-glycylserine and N-glycylhistidine.

4. The ophthalmic composition according to claim 1, wherein the dipeptide is present from 0.1 wt. % to 1.0 wt. %.

5. An ophthalmic composition comprising:
a dipeptide comprising a glycine moiety and another amino acid moiety other than glycine, wherein the dipeptide is present in an amount to enhance the biocidal efficacy of the ophthalmic composition;
an antimicrobial component selected from the group consisting of biguanides, polymeric biguanides, quaternium ammonium compounds and any one mixture thereof; and
0.005 wt. % to 0.8 wt. % of a comfort agent selected from the group consisting of hyaluronic acid, hydroxypropylmethyl cellulose, hydroxyethyl cellulose, dexpanthenol, sorbitol, propylene glycol and hydroxypropyl guar.

6. The ophthalmic composition of claim 5 further comprising
0.05 wt. % to 1 wt. % of an amphoteric surfactant of general formula I

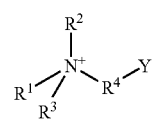

wherein $R^1$ is R or $-(CH_2)_n-NHC(O)R$, wherein R is a $C_8$-$C_{30}$ alkyl optionally substituted with hydroxyl and n is 2, 3 or 4; $R^2$ and $R^3$ are each independently selected from the group consisting of hydrogen and $C_1$-$C_4$alkyl; $R^4$ is a $C_2$-$C_8$alkylene optionally substituted with hydroxyl; and Y is $CO_2^-$ or $SO_3^-$.

7. The composition of claim 5 wherein the comfort agent is hyaluronic acid, which is present from 0.005 wt. % to 0.04 wt. %, and the antimicrobial component includes 0.3 ppm to 2.0 ppm of poly(hexamethylene biguanide).

8. The composition of claim 6 wherein $R^1$ is R; $R^2$ and $R^3$ are each independently selected from a $C_1$-$C_2$alkyl; $R^4$ is a $C_2$-$C_4$alkylene and Y is $SO_3^-$.

9. The composition of claim 5 wherein the antimicrobial component is α-[4-tris(2-hydroxyethyl)-ammonium chloride-2-butenyl]poly[1-dimethyl ammonium chloride-2-butenyl]-ω-tris(2-hydroxyethyl) ammonium chloride, which is present from 0.5 ppm to 15 ppm.

10. The composition of claim 5 further comprising 0.01 wt. % to 0.05 wt. % ethylenediaminetetraacetic acid or a corresponding salt thereof.

11. The composition of claim 5 wherein the comfort agent is propylene glycol, sorbitol or hydroxypropylmethyl cellulose.

12. The composition of claim 5 wherein the comfort agent is hydroxypropyl guar.

13. The ophthalmic composition of claim 5 further comprising a poloxamine with an HLB value from 13 to 28.

14. A method of cleaning and disinfecting a contact lens, the method comprising soaking the contact lens in the ophthalmic composition of claim 5 for at least two hours.

15. The method of claim 14 further comprising inserting the cleaned and disinfected contact lens into the eye without rinsing the lens after soaking.

16. The method of claim 14 further comprising rinsing the cleaned and disinfected contact lens with the composition of claim 5 prior to inserting the lens into the eye.

* * * * *